(12) United States Patent
Corbett (10) Patent No.: US 10,427,163 B2
(45) Date of Patent: Oct. 1, 2019

(54) CUVETTE CARRIER

(71) Applicant: Malvern Panalytical Limited, Malvern, Worcestershire (GB)

(72) Inventor: Jason Corbett, Malvern (GB)

(73) Assignee: Malvern Panalytical Limited, Malvern, Worcestershire (GB)

( * ) Notice: Subject to any disclaimer, the term of this patent is extended or adjusted under 35 U.S.C. 154(b) by 0 days.

(21) Appl. No.: 15/750,971

(22) PCT Filed: Sep. 20, 2016

(86) PCT No.: PCT/GB2016/052924
§ 371 (c)(1),
(2) Date: Feb. 7, 2018

(87) PCT Pub. No.: WO2017/051161
PCT Pub. Date: Mar. 30, 2017

(65) Prior Publication Data
US 2018/0236452 A1    Aug. 23, 2018

(30) Foreign Application Priority Data

Sep. 23, 2015 (GB) .................................. 1516851.1

(51) Int. Cl.
*B01L 9/06* (2006.01)
*G01N 21/03* (2006.01)
*G01N 15/02* (2006.01)
*G01N 21/51* (2006.01)
*G01N 15/00* (2006.01)
*G01N 21/47* (2006.01)

(52) U.S. Cl.
CPC ............ *B01L 9/06* (2013.01); *G01N 15/0211* (2013.01); *G01N 21/03* (2013.01);
(Continued)

(58) Field of Classification Search
CPC ............... B01L 9/06; B01L 2300/0858; B01L 2300/0654; G01N 15/0211; G01N 21/03;
(Continued)

(56) References Cited

U.S. PATENT DOCUMENTS

| 6,016,193 A | 1/2000 | Freeman et al. |
| 2008/0079939 A1* | 4/2008 | Fiolka ....................... G01J 1/04 356/364 |
| 2010/0238436 A1 | 9/2010 | Havard |
| 2014/0050619 A1 | 2/2014 | Meller |

FOREIGN PATENT DOCUMENTS

| WO | WO-03/023375 | 3/2003 |
| WO | WO-2007/126389 | 11/2007 |
| WO | WO-2014/065694 | 5/2014 |

OTHER PUBLICATIONS

Glidden et al. (Apr. 2012) "Characterizing Gold Nanorods in Solution Using Depolarized Dynamic Light Scattering." *Journal of Physical chemistry C* 116(14): 8128-8137.
(Continued)

*Primary Examiner* — Hina F Ayub
(74) *Attorney, Agent, or Firm* — Morrison & Foerster LLP (57) ABSTRACT

A cuvette carrier comprising: a plurality of walls defining a holding volume for a cuvette; a first and second transmissive region included in the plurality of walls; and a first optical polarizer arranged to polarize light passing through the first transmissive region.

13 Claims, 4 Drawing Sheets

(52) U.S. Cl.
CPC ............... *B01L 2300/0654* (2013.01); *B01L 2300/0858* (2013.01); *G01N 21/51* (2013.01); *G01N 2015/0053* (2013.01); *G01N 2015/0222* (2013.01); *G01N 2021/0367* (2013.01); *G01N 2021/4792* (2013.01); *G01N 2021/513* (2013.01)

(58) Field of Classification Search
CPC ........... G01N 21/51; G01N 2015/0053; G01N 2015/0222; G01N 2021/0367; G01N 2021/4792; G01N 2021/513
See application file for complete search history.

(56) References Cited

OTHER PUBLICATIONS

Ocean Optics Instruction Manual. (2011) "qpod: Temperature-Controlled Sample Compartment for Fiber Optic Spectroscopy," located at <http://oceanoptics.com/wp-content/uploads/qpod-manual.pdf> visited on Dec. 8, 2016, 14 pages.

Pike Technologies Product Date Sheet. (2013) "Falcon UV-VIS—Precise Cell Temperature Control Accessory," located at <http://www.piketech.com/files/pdfs/FalconPDS1413.Pdf> visited on.Dec. 8, 2016, 1 page.

International Search Report and Written Opinion dated Dec. 22, 2016, directed to International Application No. PCT/GB2016/052924; 13 pages.

\* cited by examiner

CUVETTE CARRIER

REFERENCE TO RELATED APPLICATIONS

This application is a national stage application under 35 USC 371 of International Application No. PCT/GB2016/052924, filed Sep. 20, 2016, which claims the priority of GB App. No. 1516851.1, filed Sep. 23, 2015, the entire contents of which are incorporated herein by reference.

FIELD OF THE INVENTION

The invention relates to a carrier for holding sample cuvettes, in particular to a cuvette carrier having an optically polarising component.

BACKGROUND OF THE INVENTION

Dynamic light scattering (DLS) is a powerful technique for measuring the size of particles, for example nanomaterials and nanoparticulates. Typically, a suspension or solution containing the particles is placed in a transparent sample cuvette and is illuminated with a vertically polarised laser beam. Light scattered from the particles along a particular direction is detected in a plane orthogonal to the polarisation of the incoming light, and analysed using well known methods to determine properties of the particles. Light that is scattered in any direction from the particles may be detected, such as forward-scattered light, back scattered light and/or side-scattered light (e.g. scattered light at an angle of 90° to the incoming light).

A further development of dynamic light scattering, depolarised dynamic light scattering (DDLS), seeks to quantify the anisotropy in scattering from particles that deviate from a sphere of uniform refractive index, such as rods, ellipsoids, discs, or spherical Janus particles. In DDLS, a particular polarisation of scattered light is detected. For example, a sample may be illuminated with vertically polarised light, and the correlation function of the scattered light detected in each scattered polarisation, separately, along the detection path.

There are many laboratory instruments available that can perform dynamic light scattering, such as the Malvern Zetasizer® range. However, these instruments may not be able to measure different polarisation states of the scattered light, and so cannot perform depolarised dynamic light scattering measurements. Upgrading system hardware, or replacing a system altogether in order to perform DDLS may be undesirably expensive.

SUMMARY OF THE INVENTION

In accordance with a first aspect of the invention there is provided a cuvette carrier comprising a plurality of walls defining a holding volume for a cuvette; a first and second transmissive region included in the plurality of walls; and a first optical polariser arranged to polarise light passing through the first transmissive region.

The term "polariser" as used herein refers to a filter that passes a component of light with a specific polarisation, and blocks (at least partially) components of light with other polarisations. The term "polarise" refers to filtering light with a polariser so as to preferentially pass components of light with a specific polarisation, while at least partially blocking components of light with other polarisations.

The second transmissive region may be for illuminating a region within the holding volume, and the first transmissive region may be for detecting scattered light from the said region.

Such a cuvette carrier may be used to retrofit existing equipment to allow DDLS measurements to be performed using the optical polariser to detect the polarisation of the scattered light. In particular, the cuvette carrier may fit into the cuvette holder of an existing DLS measurement system. A cuvette containing a sample may then be put into the cuvette carrier.

In some embodiments, the cuvette carrier may additionally comprise a second optical polariser arranged to polarise light passing through the second transmissive region. An axis of polarisation of the first optical polariser may be orthogonal to an axis of polarisation of the second optical polariser, or may be parallel to an axis of polarisation of the second optical polariser.

The second optical polariser may be used, for example, to polarise light entering a cuvette in the cuvette carrier, before the light is scattered by a sample in the cuvette. Alternatively the second optical polariser may be used in conjunction with the first polariser to detect the polarisation of light scattered by the sample.

The first transmissive region and second transmissive region may be located in a first wall of the plurality of walls. This may be particularly useful when the first polariser is used to detect the polarisation of backscattered light from a sample, and the second polariser used to polarise the light beam entering the sample.

In some embodiments, the cuvette carrier may further comprise a third transmissive region located in a second wall of the plurality of walls; and a third optical polariser arranged to polarise light passing through the third transmissive region. In some embodiments, an axis of polarisation of the third optical polariser may be orthogonal to an axis of polarisation of the first optical polariser, or may be parallel to an axis of polarisation of the first optical polariser. The third optical polariser may be used, for example, to polarise side-scattered light scattered by a sample that has been illuminated through the second transmissive region. A detector, for example a detector in a DLS instrument, may then detect the polarised side-scattered light as part of a DDLS experiment.

Additionally, the cuvette carrier may comprise fourth transmissive region, and optionally a fourth optical polariser arranged to polarise light passing through the fourth transmissive region. For example, the fourth transmissive region may provide means for illuminating a region within the holding volume, and the third transmissive region for detecting scattered light from the illuminated region within the holding volume.

In some such embodiments, an axis of polarisation of the fourth optical polariser may be parallel to an axis of polarisation of the second optical polariser.

The fourth transmissive region may be located in the second wall. In one example of use of a cuvette carrier according to this embodiment, the second and fourth transmissive regions may be used as windows for light entering a cuvette. The first and third polarisers may be used to polarise back-scattered light resulting from the interaction of a light beam with a sample in the cuvette carrier, the light beam having entered the cuvette carrier through the second and fourth transmissive regions respectively. In particular, the polarisation axes of the first and third polarisers may be aligned orthogonally to each other, for example so that one polariser of the cuvette carrier may transmit only the horizontal component of scattered light, and another polariser may transmit only the vertical component of scattered light. The polarisation of light entering the cuvette carrier via the second and fourth transmissive regions may be controlled by the inclusion of the second and fourth optical polarisers, aligned to have parallel axes of polarisation so that the sample is always illuminated with light of the same polarisation.

By rotating the cuvette carrier, both components of the scattered light may be detected, and so a full DDLS measurement may be performed in a retrofitted system.

In some embodiments, the first wall may be adjacent to the second wall. This may be the case, for example, when the back-scattered light is to be measured as discussed above. Alternatively, the first wall may be opposite the second wall. This set-up may be used for example to detect the polarisation of forward scattered light: light passing through the second transmissive region and forward scattered by the sample may pass through and be polarised by the third optical polariser, and light passing through the fourth transmissive region and forward scattered by the sample may pass through and be polarised by the first optical polariser. The polarised light may then be detected by a detector, for example a detector in a DLS instrument.

In some embodiments, the fourth transmissive region may be located in a third wall, wherein the third wall is opposite to the second wall. This set-up may be used, for example to detect the polarisation of side-scattered light. For example, light passing through the second transmissive region and side-scattered by the sample may pass through and be polarised by the third optical polariser, and light passing through the fourth transmissive region and side-scattered by the sample may pass through and be polarised by the first optical polariser. The polarised light may then be detected by a detector, for example a detector in a DLS instrument.

In some embodiments, each transmissive region may be located in a different wall of the plurality of walls. For example, the first transmissive region may be opposite to the third transmissive region, and the second transmissive region opposite to the fourth transmissive region.

In some embodiments, at least one of the first, second, third, or fourth transmissive regions may comprise an aperture in a wall. Alternatively, any of the transmissive regions may comprise an optical component, for example a window or lens. At least one of the first, second, third, or fourth optical polarisers may be arranged to polarise all of the light passing through the first, second, third or fourth transmissive region respectively.

The first and second transmissive regions may be adjacent to each other so as to form a continuous transmissive region. For example, the first and second transmissive regions may comprise separate parts of a single aperture in the first wall. Similarly, the third and fourth transmissive regions may be adjacent to each other so as to form a continuous transmissive region.

The optical polariser or optical polarisers may be configured to transmit light from the ultraviolet, visible, or near infrared regions of the electromagnetic spectrum, for example light with a wavelength in the range 280-2000 nm.

In some embodiments, the plurality of walls may define a substantially cuboidal holding volume. The holding volume may be adapted to receive a standard size cuvette, for example a 10 mm×10 mm sample cuvette. The cuvette carrier may further comprise an insert adapted to removably fit into the holding volume, the insert comprising a plurality of walls defining an inner volume that is smaller than the holding volume. For example, inner dimensions of the inner volume of the insert may be approximately 3 mm×3 mm. The insert may allow the cuvette carrier to be compatible with different sizes of cuvettes or smaller glass capillaries. For example, large cuvettes may fit into the holding volume without the insert being inserted into the holding volume, whereas smaller cuvettes may require the insert to be inserted into the holding volume, the smaller cuvettes being held by the insert.

The exterior shape of the cuvette carrier may be substantially cuboidal. An external horizontal cross-region of the cuvette carrier may have dimensions of approximately 12.5 mm×12.5 mm. These dimensions match the dimensions of a standard large cuvette, and so a cuvette carrier of these dimensions may fit into the cuvette holder of an existing DLS system, allowing easy retrofitting of the DLS system.

The plurality of walls may comprise a metal, for example aluminium or stainless steel. The plurality of walls may be substantially covered in a protective coating. For example, if the plurality of walls comprise aluminium, and the protective coating may be an anodised layer. A metal construction aids thermal contact with the cell area of an existing DLS system.

In some embodiments, the cuvette carrier may further comprise a narrow band filter arranged to filter light passing through the first and/or third transmissive regions. In particular, the narrow band filter may be adapted to allow transmission of light at the same wavelength as the illuminating light source for the DLS measurement. The narrow band filter may for example allow transmission of light within a range of ±1 nm of the wavelength of the illuminating light source. This may be useful for excluding fluorescent light, which may otherwise introduce noise into a DLS measurement.

In some embodiments, at least one of the optical polarisers may be configured to be removable by a user. For example a user may replace an optical polariser with a different optical polariser, or may rotate an optical polariser in order to rotate the axis of polarisation of the polariser.

According to a second aspect of the invention there is provided an apparatus for measuring particle size distribution of a sample by light scattering comprising: a light source for generating a beam of light; a cuvette according to any embodiment of the first aspect of the invention; and a detector for detecting scattered light.

According to a third aspect of the invention there is provided a method of testing the optical properties of a liquid sample, the method comprising: placing the sample in a cuvette; placing the cuvette in a cuvette carrier, the cuvette carrier comprising a plurality of walls defining a holding volume for a cuvette, a first and second transmissive region included in the plurality of walls, and a first optical polariser arranged to polarise light passing through the first transmissive region; illuminating the sample with a test beam from a light source, the test beam passing through the second transmissive region of the cuvette carrier; and detecting light scattered from the sample that passes through the first optical polariser.

In some embodiments, light that is back-scattered, side-scattered, or forward-scattered from the sample may be detected.

The method may further comprise replacing the first optical polariser with a replacement optical polariser, the replacement optical polariser having an axis of polarisation that is orthogonal to the axis of polarisation of the first optical polariser; and detecting light scattered from the sample that passes through the replacement optical polariser.

Alternatively, the cuvette carrier may further comprise a third transmissive region, a fourth transmissive region, and third optical polariser arranged to polarise light passing through the third transmissive region, the method further comprising; rotating the cuvette carrier such that the test beam passes through the fourth transmissive region of the cuvette carrier; and detecting light scattered from the sample that passes through the third optical polariser. In this way both horizontal and vertical components of scattered light may be detected, and used for depolarised dynamic light scattering analysis.

BRIEF DESCRIPTION OF THE DRAWINGS

The invention is described in further detail below by way of example and with reference to the accompanying drawings, in which:

FIG. 2b is a schematic representation of the same embodiment of cuvette carrier as in FIG. 2a, rotated by 90° compared to FIG. 2a;

DETAILED DESCRIPTION OF THE INVENTION

Figure 1:
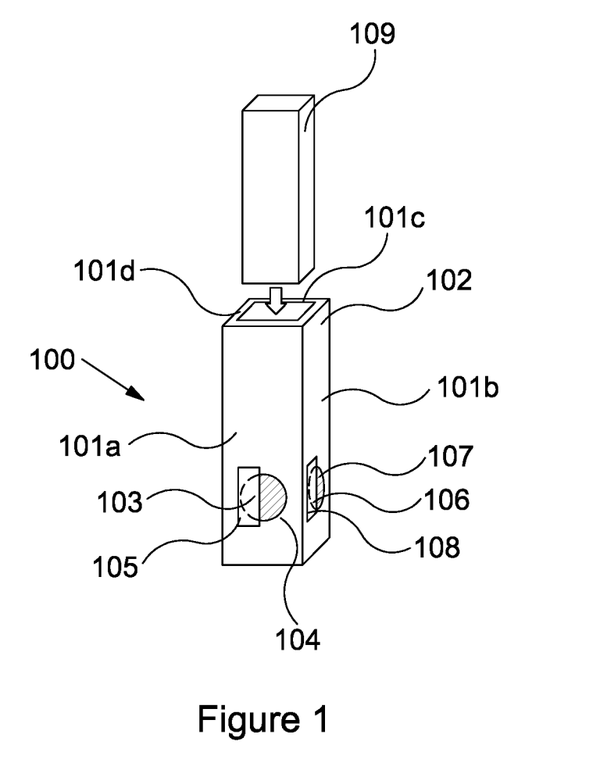
FIG. 1 is a schematic representation of a cuvette carrier according to the first aspect of the invention, with a cuvette for placing into the cuvette carrier.

FIG. 1 shows an exemplary embodiment of a cuvette carrier 100 according to the first aspect of the invention. Cuvette carrier 100 comprises a plurality of walls 101a-d that define a holding volume 102. In the illustrated embodiment, cuvette carrier 100 comprises four walls of equal width, arranged to form a holding volume 102 with a square shaped cross-section. However, in other embodiments, other numbers of walls are possible, forming otherwise shaped holding volumes. For example, cuvette carrier 100 may comprise 1, 2, 3, 5, or 6 walls. The walls 101 may be of equal widths, or may be of different widths.

A first wall 101a of the plurality of walls comprises a first transmissive region 103 (shown by a dotted line in FIG. 1) and a second transmissive region 104. A first polarising filter 105 entirely covers the first transmissive region 103, so that any light passing through the first transmissive region 103 passes through the first polarising filter 105. In this embodiment, the second transmissive region 104 is an aperture in the wall 101a, allowing light to pass into the holding volume 102. In the illustrated embodiment, the first transmissive region 103 and the second transmissive region 104 form a single aperture through the first wall 101a, but in other embodiments these regions may be separated.

A second wall 101b of the plurality of walls comprises a third transmissive region 106 (shown by a dotted line in FIG. 1) and a fourth transmissive region 107. A third polarising filter 108 entirely covers the third transmissive region 106, so that any light passing through the third transmissive region 106 passes through the third polarising filter 108. In the illustrated embodiment, the third and fourth transmissive regions 106, 107 form a single aperture in the second wall 101b, similar to the first and second transmissive regions 103, 104 in the first wall 101a.

A third wall 101c of the plurality of walls may comprise a fifth transmissive region 111 (not shown in FIG. 1, but visible in FIG. 2B) for allowing a light beam entering the cuvette carrier 100 through the second transmissive region 104 to exit the cuvette carrier 100 (for instance to avoid reflections of the light beam from contributing to optical noise in a measurement of scattered light). Similarly, a fourth wall 101d of the plurality of walls may comprise a sixth transmissive region (not shown), for allowing a light beam entering the cuvette carrier 100 through the fourth transmissive region 107 to exit the cuvette carrier 100

It is not essential for a fifth transmissive region 111 to be provided opposite the second transmissive region 104, or for a sixth transmissive region to be provided opposite the fourth transmissive region. In an alternative arrangement a reflector element may instead be provided within the cuvette carrier 100, arranged to cause a light beam entering the cuvette carrier 100 via the second transmissive region to exit the cuvette carrier via the second transmissive region (or the fourth transmissive region, or any other suitable transmissive region), and a similar reflector may be provided, arranged to cause a light beam entering the cuvette carrier 100 via the fourth transmissive region to exit the cuvette carrier via the fourth transmissive region (or the second transmissive region, or any other suitable transmissive region). Other embodiments may be arranged so that a light beam entering via the second or fourth transmissive region may respectively exit the cuvette carrier via the fourth or second transmissive region.

The cuvette carrier 100 may be used to investigate the depolarised dynamic light scattering (DDLS) properties of a sample in a cuvette 109. A cuvette 109 may be placed into the holding volume 102. The cuvette carrier 100 may then be placed in a DLS instrument, such that a beam from a light source illuminates the sample in the cuvette 109. For example, the cuvette carrier 100 may be placed in a cuvette carrier of an existing DLS system so as to retrofit the DLS system for DDLS measurements.

Figure 2A:
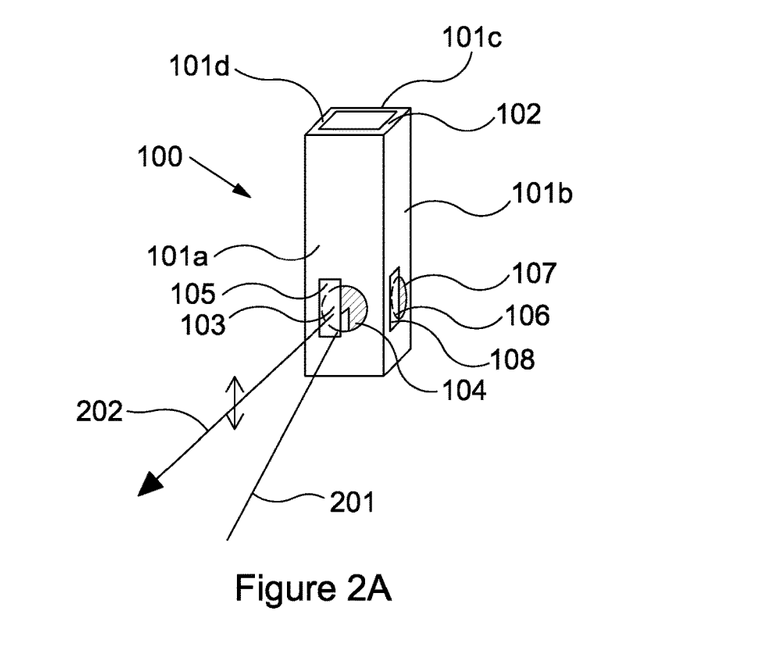
FIG. 2a is a schematic representation of an embodiment of a cuvette carrier.
Figure 2B:
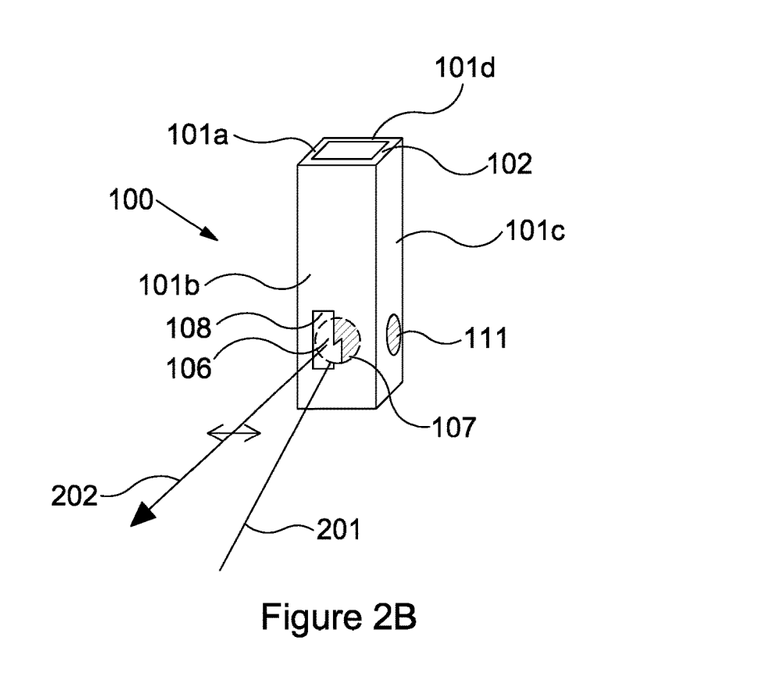

FIGS. 2A and 2B illustrate one way in which the cuvette carrier shown in FIG. 1 may be used for DDLS measurements. In this embodiment, the first polarising filter 105 is aligned so that it polarises light orthogonally to the direction of polarisation of light passing through the third polarising filter 108. For example, the first polarising filter 105 may polarise light vertically, and the third polarising filter 108 may polarise light horizontally. These directions are represented by the arrows on the scattered light beams 202 in FIGS. 2A and 2B.

FIG. 2A shows a first step of the measurements. Incoming light 201 from an external light source is used to illuminate the sample in the cuvette carrier. The light source may be, for example, a laser, for example a laser that is part of an existing DLS experimental system. The light source may provide light with a wavelength that is in the range of 280 to 2000 nm.

Incoming light 201 passes through the second transmissive region 104, and enters the holding volume 102. Particles in sample held in the holding volume 102 may scatter the light. The light may be scattered in any direction, however in the particular embodiment illustrated only backscatted light is measured—e.g. light that is scattered within a range of 160°-200° from the direction of the incoming light 201. The back-scattered light 202 passes through the first transmissive region 103, and is polarised by the first optical polariser 105. Substantially only the component of scattered light 202 that is polarised in the same direction of the axis of polarisation of the first optical polariser 105 will pass through the optical polariser 105. In the illustrated embodiment, only the vertically polarised component of the back-scattered light 202 passes through the polariser 105, and may be detected by a detector. The detector may, for example, be a photodiode, and may be the detector of an existing DLS instrument.

The incoming light 201 passing through the second transmissive region 104 may exit the holding volume 102 via the fifth transmissive region 111.

The horizontally polarised component of the scattered light may be measured. This is shown in FIG. 2B. The cuvette carrier 100 may be rotated by 90° so that the second wall 101b faces the illuminating light 201. This may be achieved manually, for example by removing the cuvette carrier 100 from a cuvette holder of a DLS system, rotating the cuvette carrier 100 by 90°, and replacing the cuvette carrier 100 in the cuvette holder. Alternatively a motor may be used to automatically rotate the cuvette carrier 100. Alternatively the cuvette carrier 100 may be held fixed, but the direction of the incoming light 201 rotated by 90° so that the second wall 101b is illuminated.

In FIG. 2B, the incoming light 201 passes through the fourth transmissive region 107, and is scattered by the sample in the holding volume 104. Again, in the illustrated embodiment only back-scattered light is measured. Back-scattered light 202 passes through the third transmissive region 106, and is polarised by the third optical polariser 108, so that only the horizontally polarised component of the back-scattered light 202 passes through the polariser 108. This light may then be detected by a detector.

The incoming light 201 passing through the fourth transmissive region 107 may exit the holding volume 102 via the sixth transmissive region (not shown).

In this way, both the vertical and horizontal components of scattered light may be measured. Combining these measurements, the polarisation of the back-scattered light may be calculated, and used for DDLS calculations.

Figure 3:
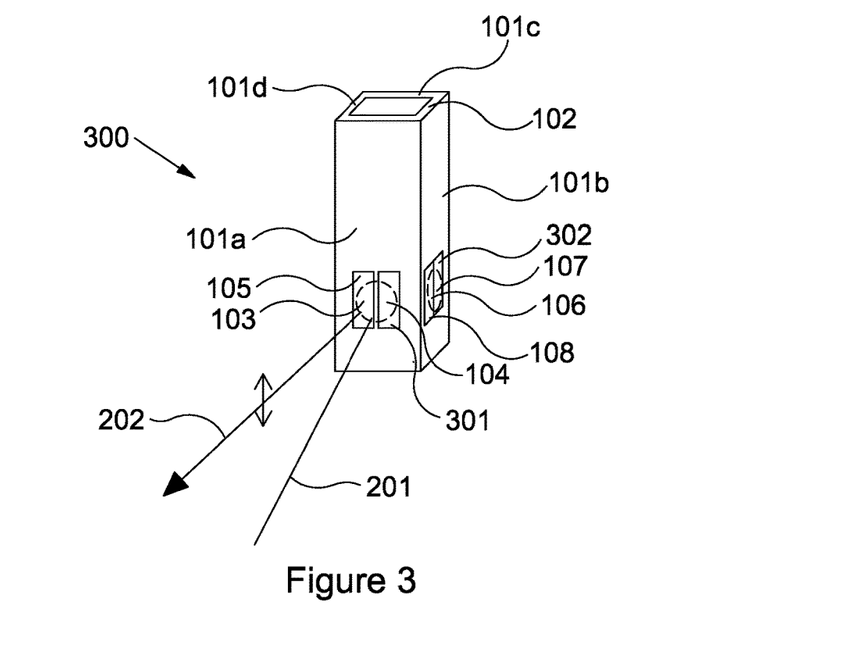
FIG. 3 is a schematic representation of an alternative cuvette carrier.

In some circumstances, it may be important to ensure that the illuminating light has a known polarisation state. This may particularly be the case if the light source is not a laser. FIG. 3 shows an alternative embodiment of a cuvette carrier 300 that may be used in such cases.

The cuvette carrier 300 comprises all of the features of cuvette carrier 100. Additionally, a second optical polariser 301 covers the second transmissive region 104, and a fourth optical polariser 302 covers the fourth transmissive region 107. The second 301 and fourth 302 optical polarisers may in particular be aligned so that they polarise light along the same axis—for example both polarisers 301, 302 may polarise light horizontally, or both polarisers 301, 302 may polarise light vertically.

Cuvette carrier 300 may be used for DDLS measurements of back-scattered light in the same way as described for cuvette carrier 100. In this case, incoming light 201 entering the second 104 or fourth 107 transmissive regions will pass through the second 301 and fourth 302 optical polarisers respectively, before entering the sample. The incoming light will therefore be polarised along a known direction.

The examples above have described the measurement of back-scattered light only. However, a skilled person will readily understand that the cuvette carrier may be adapted to detect light scattered at any angle, using a similar method to the measurements described above. For example, any of the first, second, third, and fourth transmissive regions, and their respective optical polarisers, may be located on any of the plurality of walls of the cuvette carrier, in order to detect any direction of scattered light. In particular, the first optical polariser on the first transmissive region may be used to polarise scattered light resulting from the interaction with the sample of a light beam passing through the second transmissive region, and the third optical polariser on the third transmissive region may be used to polarise scattered light resulting from the interaction with the sample of a light beam passing through the fourth transmissive region. In any embodiment, the second and fourth transmissive regions may be covered by second and fourth optical polarisers, in order to ensure a known, and common, polarisation of light entering the sample, as described above.

Figure 4:
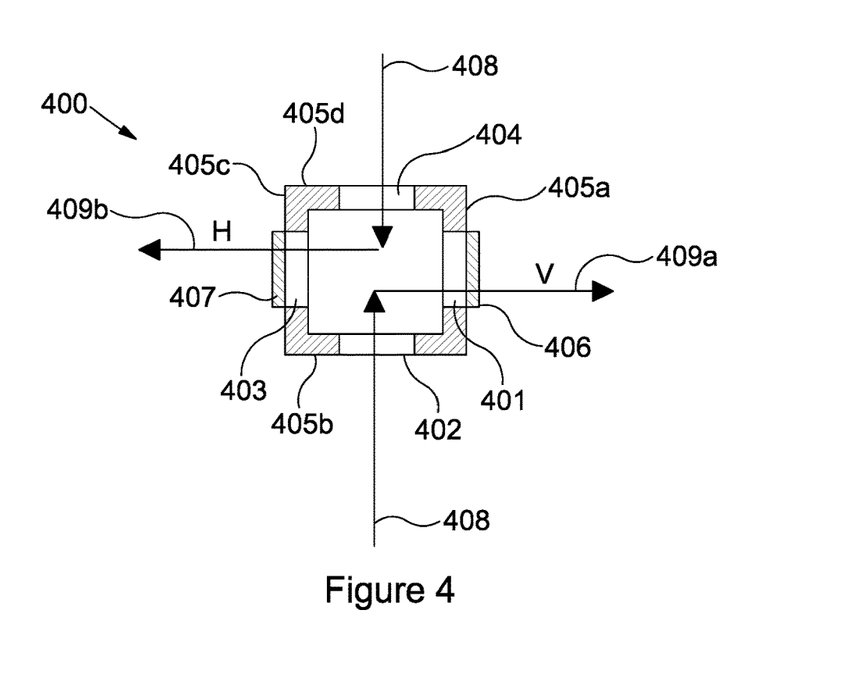
FIG. 4 is a top-down view of an embodiment of a cuvette carrier for measuring side scattered light.

For example, FIG. 4 shows an embodiment of a cuvette carrier 400 that may be used to measure side-scattered light, i.e. light that is scattered by substantially 70°-110° from the direction of incoming light. In cuvette carrier 400, each transmissive section 401-404 is located on a different wall of the plurality of walls 405a-d. The first transmissive section 401 is located on a first wall 405a. The second transmissive section 402 is located on a second wall 405b that is adjacent to the first wall 405a. The third transmissive section 403 is located on a third wall 405c that is opposite to the first wall 405a. The fourth transmissive section is located on a fourth wall 405d that is opposite to the second wall 405b. The second 402 and fourth 404 transmissive sections may or may not be covered by second and fourth optical polarisers.

DDLS measurements using the cuvette carrier 400 may proceed in a similar way to the method used for cuvette carrier 100. The polarisation axis of the first 406 and third 407 optical polarisers are aligned orthogonally to one another, for example the first optical polariser 406 may be aligned to transmit only vertically polarised light, and the third optical polariser may be aligned to transmit only horizontally polarised light (denoted in the figure by the V and H respectively on the scattered beams 409a and 409b).

In a first step, vertically polarised side-scattered light is measured. An incoming light beam 408 passes through the second transmissive region 402 and is scattered by a sample in the cuvette carrier 400. Side-scattered light 409a passes through the first transmissive region 401. The vertically polarised component of this side-scattered light 409a passes through the first optical polariser 406, and is detected by a detector. The incoming light beam 408 passing through the second transmissive region 402 may exit the cuvette carrier 100 via the fourth transmissive region 404.

In a second step, horizontally polarised side-scattered light is measured. The cuvette carrier is rotated 180°, so that the incoming light beam 408 passes through the fourth transmissive region 404 and is scattered by a sample in the cuvette carrier 400. Side-scattered light 409b passes through the third transmissive region 403. The incoming light beam 408 passing through the fourth transmissive region 404 may exit the cuvette carrier 100 via the second transmissive region 402. The horizontally polarised component of this side-scattered light 409b passes through the third optical polariser 407, and is detected by a detector. Thus both the vertical and horizontal components of side-scattered light are measured, and used for DDLS analysis.

Figure 5:
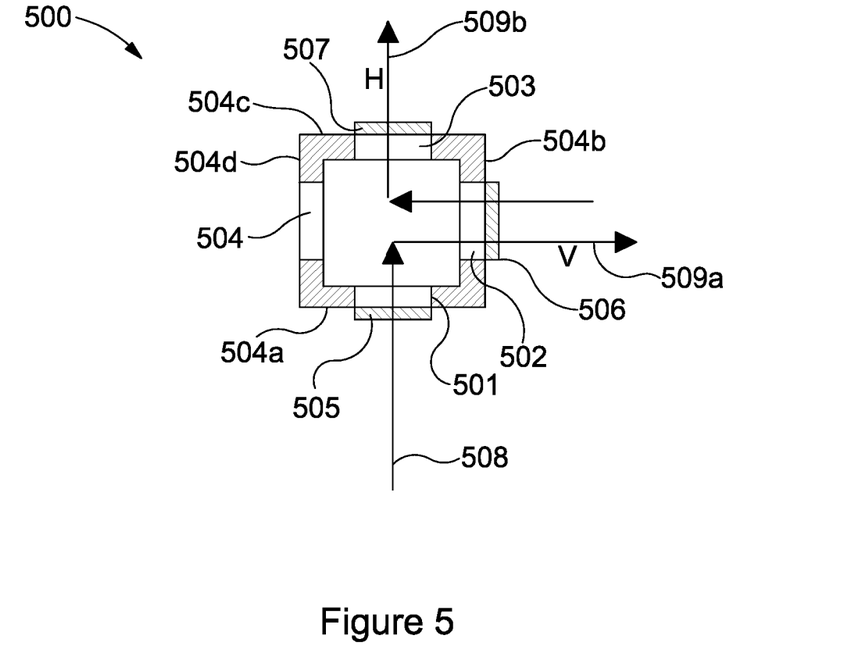
FIG. 5 is a top-down view an alternative embodiment of a cuvette carrier for measuring side scattered light.

FIG. 5 illustrates an alternative method of using a cuvette carrier 500 to measure side-scattered light. Cuvette carrier 500 comprises a first 501, second 502, third 503 and fourth 504 transmissive region, located in a first 504a, second 504b, third 505c and fourth 505d wall of the plurality of walls respectively. In this embodiment for measuring side-scatted light, the first wall 504a is adjacent to the second wall 504b, and the third wall 504c is adjacent to the second wall 504b and opposite to the first wall 504a. The fourth wall 505d is opposite to the second wall 504b.

Each transmissive section 501, 502, 503 is covered by a respective optical polariser 505, 506, 507. The fourth transmissive region 504 is not covered by an optical polariser. The first optical polariser 505 and second optical polariser 506 are aligned to polarise light along the same axis—for example vertically. The third optical polariser 507 is aligned to polarise light along an axis that is orthogonal to the axis of the first 505 and second 506 polarisers—for example horizontally.

For DDLS measurements, the cuvette carrier 500 is first arranged so that incoming light 508 passes through the first optical polariser 505 and first transmissive region 501, ensuring that the light entering the sample is vertically polarised, in this example. The light is then side-scattered by the particles in the sample. The incoming light 508 entering the cuvette via the first transmissive region 501 that is not scattered from the sample exits the cuvette carrier 500 via the third transmissive region 503. Side-scattered light 509a passes through the second transmissive region 502, and is polarised by the second polariser 506 so that only vertically polarised side-scattered light 509a passes through the second polariser and is detected by a detector.

To measure the horizontal component of side-scattered light, the cuvette carrier 500 may be rotated by 90°, so that incoming light 508 now enters the sample through the second transmissive region 502. The second optical polariser 502 will ensure that only vertically polarised incoming light 508 is transmitted into the sample. The incoming light 508 entering the cuvette via the second transmissive region 502 that is not scattered from the sample exits the cuvette carrier 500 via the fourth transmissive region 504. Light that is side-scattered by the sample then passes through the third transmissive region 503. The third optical polariser 507 only allows the horizontal component of the side-scattered light 509b to be transmitted, which is then detected by a detector. Thus the vertical and horizontal components of side-scattered light may be measured using only three transmissive regions.

It is to be understood that the above embodiments are only examples of cuvette carriers according to this invention, and that many other embodiments of cuvette carriers, and methods of using them for DDLS measurements, are possible within the scope of the invention. In particular, the arrangement of transmissive regions may be chosen to measure light that is scattered at any angle, including back-scattered, side-scattered, and forward-scattered light. A cuvette carrier may comprise more than four transmissive regions, and respective optical polarisers, to enable a single cuvette carrier to be used to measure different directions of scattered light. The optical polarisers may be removable or changeable by the user. For example the second and fourth polarisers may be removable, or any orientation of any of the polarisers may be changed to rotate their polarisation axis.

Additionally, any embodiment may further comprise at least one narrow band filter covering at least one of the transmissive regions, and in particular transmissive regions that are in the path of the scattered light to be detected. The narrow band filter may allow transmission of light with a wavelength in the range of ±1 nm of the wavelength of the illuminating light source. The narrow band filter may be required in cases where the sample fluoresces under illumination by the light source. Fluorescent light is uncorrelated, and therefore degrades the DLS measurement. The narrow band filter may substantially remove the fluorescent light from the scattered light beam. The narrow band filters may be removable by the user, so that unnecessary loss due to the filters is avoided when the sample does not fluoresce at the illumination wavelength.

Other embodiments are intentionally within the scope of the invention as defined by the appended claims.

The invention claimed is:

1. An apparatus comprising:
   a cuvette carrier comprising:
   a plurality of walls defining a holding volume for a cuvette;
   a first and second transmissive region included in the plurality of walls; and
   a first optical polariser arranged to polarise light passing through the first transmissive region;
   wherein the first transmissive region and second transmissive region are located in a first wall of the plurality of walls, and the cuvette carrier is for performing a depolarised dynamic light scattering measurement on a sample within a cuvette that is within the cuvette carrier, with the sample illuminated through the second transmissive region, and scattered light detected through the first transmissive region.

2. The apparatus of claim 1, further comprising a second optical polariser arranged to polarise light passing through the second transmissive region, the axis of polarisation of the first optical polariser is orthogonal to an axis of polarisation of the second optical polariser.

3. The apparatus of claim 1, further comprising:
   a third transmissive region located in a second wall of the plurality of walls; and
   a third optical polariser arranged to polarise light passing through the third transmissive region.

4. The apparatus of claim 3, wherein an axis of polarisation of the third optical polariser is orthogonal to an axis of polarisation of the first optical polariser.

5. The apparatus of claim 3, further comprising a fourth transmissive region.

6. The apparatus of claim 5, wherein the apparatus is configured to perform:
   a first measurement in which the beam of light from the light source passes through the second transmissive region and the detector detects scattered light that passes through the first optical polariser; and
   a second measurement in which the cuvette carrier is rotated such that the beam of light passes through the fourth transmissive region, and the detector detects scattered light that passes through the third optical polariser.

7. The apparatus of claim 5, further comprising a fourth optical polariser arranged to polarise light passing through the fourth transmissive region.

8. The apparatus of claim 5, wherein the fourth transmissive region is located in the second wall.

9. The apparatus of claim 5, wherein at least one of the first, second, third, or fourth transmissive regions comprises an aperture in a wall.

10. The apparatus of claim 5, wherein the third and fourth transmissive regions are adjacent to each other so as to form a continuous transmissive region.

11. The apparatus of claim 3, wherein the first wall is adjacent to the second wall.

12. The apparatus of claim 1, wherein the first and second transmissive regions are adjacent to each other so as to form a continuous transmissive region.

13. The apparatus of claim 1, further comprising an insert adapted to fit into the holding volume, the insert comprising a plurality of walls defining an inner volume that is smaller than the holding volume.

\* \* \* \* \*